US010159837B2

(12) United States Patent
Lee et al.

(10) Patent No.: US 10,159,837 B2
(45) Date of Patent: *Dec. 25, 2018

(54) PREFERENTIAL THERAPEUTIC MODULATION WITHOUT PATIENT-PERCEIVED PARESTHESIA

(71) Applicant: Boston Scientific Neuromodulation Corporation, Valencia, CA (US)

(72) Inventors: Dongchul Lee, Agua Dulce, CA (US); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/679,993

(22) Filed: Apr. 6, 2015

(65) Prior Publication Data

US 2015/0209587 A1     Jul. 30, 2015

Related U.S. Application Data

(63) Continuation of application No. 13/843,102, filed on Mar. 15, 2013, now Pat. No. 9,002,459.

(60) Provisional application No. 61/703,195, filed on Sep. 19, 2012.

(51) Int. Cl.
    *A61N 1/36*     (2006.01)
    *A61N 1/05*     (2006.01)

(52) U.S. Cl.
    CPC ....... *A61N 1/36071* (2013.01); *A61N 1/0551* (2013.01); *A61N 1/36171* (2013.01); *A61N 1/36175* (2013.01); *A61N 1/0553* (2013.01)

(58) Field of Classification Search
    CPC ............ A61N 1/36071; A61N 1/36175; A61N 1/36171
See application file for complete search history.

(56) References Cited

U.S. PATENT DOCUMENTS

| 6,516,227 | B1 | 2/2003 | Meadows et al. |
|---|---|---|---|
| 6,675,046 | B2 | 1/2004 | Holsheimer |
| 6,895,280 | B2 | 5/2005 | Meadows et al. |
| 6,993,384 | B2 | 1/2006 | Bradley et al. |
| 7,317,948 | B1 | 1/2008 | King et al. |
| 7,333,857 | B2 | 2/2008 | Campbell |

(Continued)

FOREIGN PATENT DOCUMENTS

| WO | WO-2006029257 A2 | 3/2006 |
|---|---|---|
| WO | WO-2006135791 A2 | 12/2006 |

OTHER PUBLICATIONS

"U.S. Appl. No. 13/843,102, Advisory Action dated Feb. 10, 2014", 3 pgs.

(Continued)

*Primary Examiner* — Mihcael Kahelin
(74) *Attorney, Agent, or Firm* — Schwegman Lundberg & Woessner, P.A.

(57) ABSTRACT

A method of providing therapy to a patient. The method comprises conveying pulsed electrical current at a defined pulse width and a defined pulse rate into spinal cord tissue. The defined pulse width is equal to or less than 200 μs, and the defined pulse rate is less than 1500 Hz, such that neural elements in the dorsal horn are modulated and/or the patient does not perceive paresthesia during the conveyance of the pulsed electrical current into the spinal cord tissue.

20 Claims, 7 Drawing Sheets

(56) References Cited

U.S. PATENT DOCUMENTS

| | | | |
|---|---|---|---|
| 7,539,538 B2 | 5/2009 | Parramon et al. | |
| 7,650,184 B2 | 1/2010 | Walter | |
| 7,979,133 B2 | 7/2011 | Feler et al. | |
| 8,019,439 B2 | 9/2011 | Kuzma et al. | |
| 8,170,675 B2 | 5/2012 | Alataris et al. | |
| 8,209,021 B2 | 6/2012 | Alataris et al. | |
| 8,224,453 B2 | 7/2012 | De Ridder | |
| 8,255,057 B2 | 8/2012 | Fang et al. | |
| 8,355,797 B2 | 1/2013 | Caparso et al. | |
| 8,359,102 B2 | 1/2013 | Alataris et al. | |
| 8,359,103 B2 | 1/2013 | Alataris et al. | |
| 8,380,318 B2 | 2/2013 | Kishawi et al. | |
| 8,396,559 B2 | 3/2013 | Alataris et al. | |
| 8,423,147 B2 | 4/2013 | Alataris et al. | |
| 8,455,716 B2 | 6/2013 | Huang et al. | |
| 8,504,147 B2 | 8/2013 | Deem et al. | |
| 8,615,300 B2 | 12/2013 | Feler et al. | |
| 8,649,874 B2 | 2/2014 | Alataris et al. | |
| 8,670,831 B2 | 3/2014 | Wacnik et al. | |
| 8,676,329 B2 | 3/2014 | Wacnik et al. | |
| 8,676,331 B2 | 3/2014 | Parker | |
| 8,731,675 B2 | 5/2014 | Ranu et al. | |
| 8,751,009 B2 | 6/2014 | Wacnik | |
| 9,002,459 B2 | 4/2015 | Lee et al. | |
| 2003/0139781 A1 | 7/2003 | Bradley et al. | |
| 2007/0150036 A1 | 6/2007 | Anderson | |
| 2007/0168004 A1 | 7/2007 | Walter | |
| 2007/0168007 A1 | 7/2007 | Kuzma et al. | |
| 2008/0188909 A1 | 8/2008 | Bradley | |
| 2009/0204173 A1 | 8/2009 | Fang et al. | |
| 2010/0010566 A1 | 1/2010 | Thacker et al. | |
| 2010/0121409 A1 | 5/2010 | Kothandaraman et al. | |
| 2010/0249875 A1 | 9/2010 | Kishawi et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2011/0184488 A1* | 7/2011 | De Ridder | A61N 1/36071 607/46 |
| 2012/0016437 A1 | 1/2012 | Alataris et al. | |
| 2012/0059446 A1 | 3/2012 | Wallace et al. | |
| 2012/0083709 A1 | 4/2012 | Parker et al. | |
| 2012/0203304 A1 | 8/2012 | Alataris et al. | |
| 2012/0253422 A1 | 10/2012 | Thacker et al. | |
| 2012/0265279 A1 | 10/2012 | Zhu et al. | |
| 2012/0283797 A1 | 11/2012 | De Ridder | |
| 2012/0290041 A1 | 11/2012 | Kim et al. | |
| 2013/0041425 A1 | 2/2013 | Fang et al. | |
| 2013/0066411 A1 | 3/2013 | Thacker et al. | |
| 2013/0116752 A1 | 5/2013 | Parker et al. | |
| 2013/0268021 A1 | 10/2013 | Moffitt | |
| 2013/0296975 A1 | 11/2013 | Lee et al. | |
| 2014/0081349 A1 | 3/2014 | Lee et al. | |

OTHER PUBLICATIONS

"U.S. Appl. No. 13/843,102, Appeal Brief filed Apr. 16, 2014", 16 pgs.
"U.S. Appl. No. 13/843,102, Examiner Interview Summary dated Oct. 7, 2013", 3 pgs.
"U.S. Appl. No. 13/843,102, Examiner Interview Summary dated Nov. 18, 2014", 3 pgs.
"U.S. Appl. No. 13/843,102, Final Office Action dated Sep. 29, 2014", 8 pgs.
"U.S. Appl. No. 13/843,102, Final Office Action dated Dec. 13, 2013", 7 pgs.
"U.S. Appl. No. 13/843,102, Non Final Office Action dated Jun. 10, 2014", 11 pgs.
"U.S. Appl. No. 13/843,102, Notice of Allowance dated Dec. 5, 2014", 8 pgs.
"U.S. Appl. No. 13/843,102, Preliminary Amendment filed Jul. 5, 2013", 5 pgs.
"U.S. Appl. No. 13/843,102, Response filed Feb. 4, 2014 to Final Office Action dated Dec. 13, 2013", 9 pgs.
"U.S. Appl. No. 13/843,102, Response filed Aug. 25, 2014 to Non Final Office Action dated Jun. 10, 2014", 9 pgs.
"U.S. Appl. No. 13/843,102, Response filed Nov. 11, 2013 to Non Final Office Action dated Oct. 15, 2013", 8 pgs.
"U.S. Appl. No. 13/843,102, Response filed Nov. 19, 2014 to Final Office Action dated Sep. 29, 2014", 10 pgs.
"Posterior horn of spinal cord", Wikipedia, [Online] retrieved from the internet: <http://en.wikipedia.org/wiki/Posterior_horn_of_spinal_cord>, (Jul. 22, 2013), 1 pgs.
Bradley, Kerry, et al., "Method for Epidural Stimulation of Neural Structures", U.S. Appl. No. 61/704,381, filed Sep. 21, 2012, 45 pgs.
Rao, Prakash, et al., "Technique for Linking Electrodes Together During Programming of Neurostimulation System", U.S. Appl. No. 61/561,760, filed Nov. 18, 2011.
Vansickle, Dennis Allen, et al., "Neuromodulation System and Method for Transitioning Between Programming Modes", U.S. Appl. No. 14/214,752, filed Mar. 15, 2014.
Vansickle, Dennis Allen, "Systems and Methods for Delivering Sub-Threshold Therapy to a Patient", U.S. Appl. No. 61/801,917, filed Mar. 15, 2013.
Brachini, J., et al., "Spinal Segmental and Supraspinal Mechanisms Underlying the Pain-Relieving Effects of Spinal Cord Stimulation: An Experimental Study in a Rat Model of Neuropathy", Neuroscience 215, (Jul. 26, 2012), 196-208.
Braz, Joao, et al., "Transmitting Pain and Itch Messages: A Contemporary View of the Spinal Cord Circuits that Generate Gate Control", Neuron 82, (May 7, 2014), 522-536.
Crosby, Nathan D., et al., "Burst and Tonic Spinal Cord Stimulation Differentially Activate GABAergic Mechanisms to Attenuate Pain in a Rat Model of Cervical Radiculopathy", IEEE Transactions on Biomedical Engineering, vol. 62, No. 6, Jun. 2015, 1604-1613.
De Ridder, Dirk, et al., "Burst and Tonic Spinal Cord Stimulation: Different and Common Brain Mechanisms", Neuromodulation 19, (2016), 47-59.
De Ridder, Dirk, et al., "Burst Spinal Cord Stimulation for Limb and Back Pain", World Neurosurgery Peer-Review Reports, (2013), 1-9.
Parker, John L., et al., "Compound action potentials recorded in the human spinal cord during neurostimulation for pain relief", Pain 153, (2012), 593-601.
Tang, Rurong, et al., "Comparison of Burst and Tonic Spinal Cord Stimulation on Spinal Neural Processing in an Animal Model", Neuromodulation 17, (2014), 143-151.
Abraira, Victoria E., et al., "The Sensory Neurons of Touch", Neuron, 79(4), (2013), 618-639.
De Ridder, Dirk, et al., "Burst and Tonic Spinal Cord Stimulation: Different and Common Brain Mechanisms", Neuromodulation, 19(1), (Dec. 2015), 47-59.
Holsheimer, Jan, et al., "Which Neuronal Elements are Activated Directly by Spinal Cord Stimulation", Neuromodulation, 5(1), (Jan. 2002), 25-31.
McIntyre, Cameron C, et al., "Selective Microstimulation of Central Nervous System Neurons", Annals of Biomedical Engineering., 28(3), (Mar. 2000), 219-233.
Rubinstein, J. T., et al., "Axon Termination Conditions for Electrical Stimulation", IEEE Transactions on Biomedical Engineering, 40(7), (1993), 654-663.
Struijk, Johannes J., et al., "Excitation of Dorsal Root Fibers in Spinal Cord Stimulation: a Theoretical Study", IEEE Transactions on Biomedical Engineering, 40(7), (Jul. 1993), 632-639.

* cited by examiner

PREFERENTIAL THERAPEUTIC MODULATION WITHOUT PATIENT-PERCEIVED PARESTHESIA

RELATED APPLICATION DATA

This application is a continuation of U.S. application Ser. No. 13/843,102, filed Mar. 15, 2013, which application claims the benefit under 35 U.S.C. § 119 to U.S. provisional patent application Ser. No. 61/703,195, filed Sep. 19, 2012. The foregoing applications are hereby incorporated by reference into the present application in their entirety.

FIELD OF THE INVENTION

The present invention relates to tissue stimulation systems, and more particularly, to a system and method for stimulating spinal nerve tissue to provide therapy to a patient.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic neuropathic pain syndromes, and the application of spinal cord stimulation has expanded to include additional applications, such as angina pectoralis, peripheral vascular disease, and incontinence, among others. Spinal cord stimulation is also a promising option for patients suffering from motor disorders, such as Parkinson's Disease, Dystonia and essential tremor.

An implantable SCS system typically includes one or more electrode-carrying stimulation leads, which are implanted at a stimulation site in proximity to the spinal cord tissue of the patient, and a neurostimulator implanted remotely from the stimulation site, but coupled either directly to the stimulation lead(s) or indirectly to the stimulation lead(s) via a lead extension. The neurostimulation system may further include a handheld patient programmer to remotely instruct the neurostimulator to generate electrical stimulation pulses in accordance with selected neuromodulation parameters. The handheld programmer may, itself, be programmed by a technician attending the patient, for example, by using a Clinician's Programmer (CP), which typically includes a general purpose computer, such as a laptop, with a programming software package installed thereon.

Thus, programmed electrical pulses can be delivered from the neurostimulator to the stimulation electrode(s) to stimulate or activate a volume of the spinal cord tissue. In particular, electrical stimulation energy conveyed to the electrodes creates an electrical field, which, when strong enough, depolarizes (or "stimulates") the neural fibers within the spinal cord beyond a threshold level, thereby inducing the firing of action potentials (APs) that propagate along the neural fibers to provide the desired efficacious therapy to the patient.

As discussed, SCS may be utilized to treat patients suffering from chronic neuropathic pain. To this end, mid- to high-frequency electrical stimulation is generally applied to large sensory afferents of the dorsal column (DC) nerve fibers at an amplitude that provides pain relief. While the full mechanisms are pain relief are not well understood, it is believed that the perception of pain signals is inhibited via the gate control theory of pain, which suggests that enhanced activity of innocuous touch or pressure afferents via electrical stimulation creates interneuronal activity within the dorsal horn that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, stimulation electrodes are typically implanted within the dorsal epidural space to provide stimulation to the DC nerve fibers.

Activation of large sensory fibers also typically creates a sensation known as paresthesia that can be characterized as an alternative sensation that replaces the pain signals sensed by the patient. Although alternative or artifactual sensations are usually tolerated relative to the sensation of pain, patients sometimes report these sensations to be uncomfortable, and therefore, they can be considered an adverse side-effect to neuromodulation therapy in some cases. Because the perception of paresthesia has been used as an indicator that the applied electrical energy is, in fact, alleviating the pain experienced by the patient, the amplitude of the applied electrical energy is generally adjusted to a level that causes the perception of paresthesia. It has been shown that high-frequency pulsed electrical energy can be effective in providing neuromodulation therapy for chronic pain without causing paresthesia. However, high-frequency pulsed electrical energy consumes an excessive amount of energy, thereby requiring the neuromodulator device to be charged more often.

There, thus, remains a need for an improved technique to treat chronic pain without using high-frequency pulsed electrical energy.

SUMMARY OF THE INVENTION

In accordance with one aspect of the present inventions, a method of providing therapy to a patient comprises conveying pulsed electrical current at a defined pulse width and a defined pulse rate into spinal cord tissue of the patient. The defined pulse width is equal to or less than 200 µs, and the defined pulse rate is less than 1500 Hz, such that neural elements (e.g., nerve endings) in the dorsal horn are modulated. In one method, the neural elements in the dorsal horn are preferentially stimulated over dorsal column fibers. The conveyance of the pulsed electrical current may stimulate neural elements of the dorsal horn by evoking action potentials in the neural elements, or may be subthreshold and not evoke action potentials in the neural elements. In one method, the defined pulse width is within the range of 10 µs-100 µs, and preferably in the range of 10 µs-50 µs. The pulsed electrical current may be anodic or cathodic. The pulsed electrical current may be conveyed into the spinal cord tissue without causing a perception of paresthesia in the patient. If the patient suffers from chronic pain, the conveyance of the pulsed electrical current into the spinal cord tissue may treat the chronic pain.

In accordance with a second aspect of the present inventions, a method of providing therapy to a patient comprises conveying pulsed electrical current at a defined pulse width and a defined pulse rate into spinal cord tissue of the patient. The defined pulse width is equal to or less than 200 µs, and the defined pulse rate is less than 1500 Hz, such that the patient does not feel paresthesia during the conveyance of the pulsed electrical current into the spinal cord tissue. In one method, the defined pulse width is within the range of 10 μs-100 μs, and preferably in the range of 10 μs-50 μs. In one method, the defined pulse rate is equal to or less than 1500 Hz, and preferably less than 500 Hz. The pulsed electrical current may be anodic or cathodic. If the patient suffers from chronic pain, the conveyance of the pulsed electrical current into the spinal cord tissue may treat the chronic pain.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
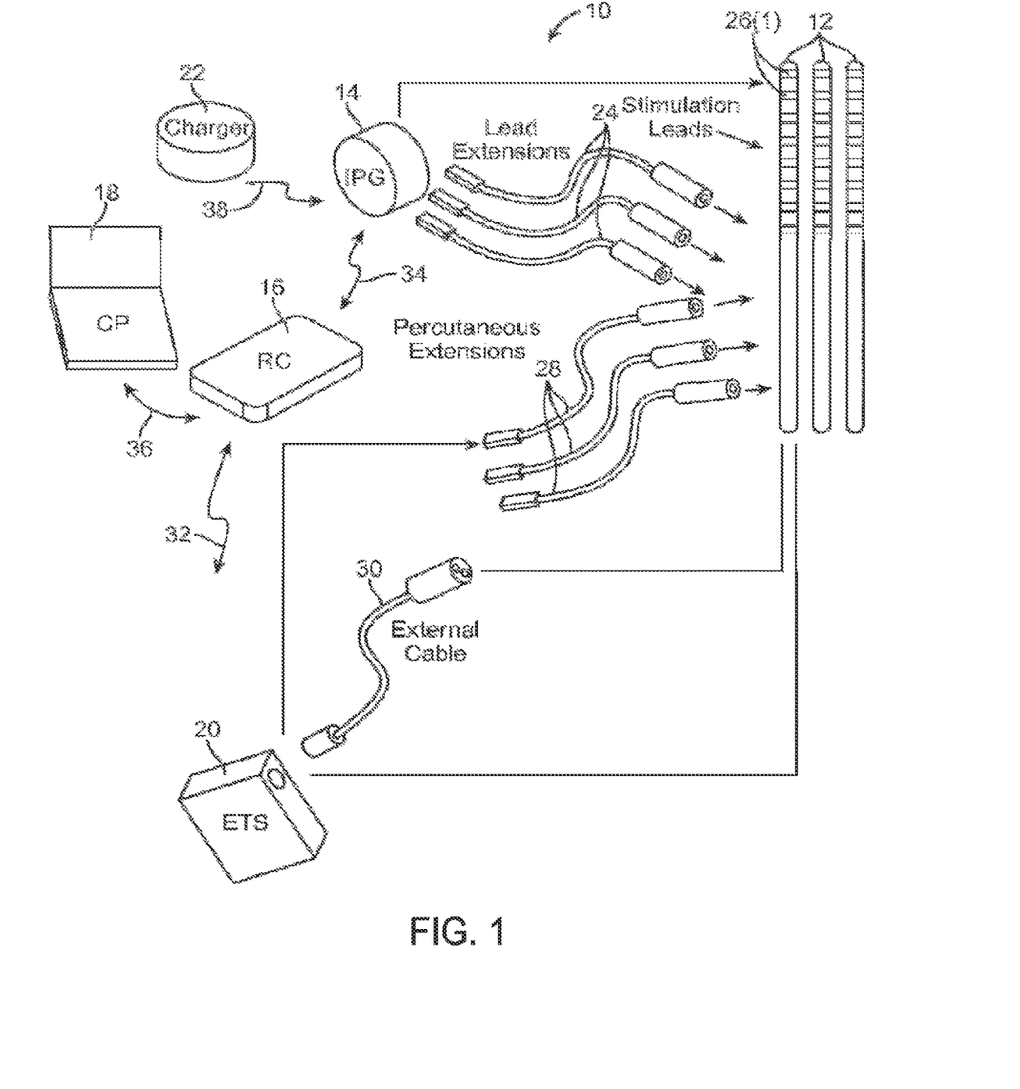
FIG. 1 is a plan view of a Spinal Cord Modulation (SCM) system constructed in accordance with one embodiment of the present inventions.

Turning first to FIG. 1, an exemplary spinal cord modulation (SCM) system 10 generally comprises a plurality of modulation leads 12 (in this case, three), an implantable pulse generator (IPG) 14 (or alternatively RF receiver-stimulator), an external remote control RC 16, a Clinician's Programmer (CP) 18, an External Trial Modulator (ETM) 20, and an external charger 22.

The IPG 14 is physically connected via one or more lead extensions 24 to the modulation leads 12, which carry a plurality of electrodes 26 arranged in an array. The modulation leads 12 are illustrated as percutaneous leads in FIG. 1, although as will be described in further detail below, a surgical paddle lead can be used in place of the percutaneous leads. As will also be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation that is to be provided. Thus, any functions described herein with respect to the IPG 14 can likewise be performed with respect to the ETM 20.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

For purposes of brevity, the details of the RC 16, CP 18, ETM 20, and external charger 22 will not be described herein. Details of exemplary embodiments of these devices are disclosed in U.S. Pat. No. 6,895,280, which is expressly incorporated herein by reference.

Figure 2:
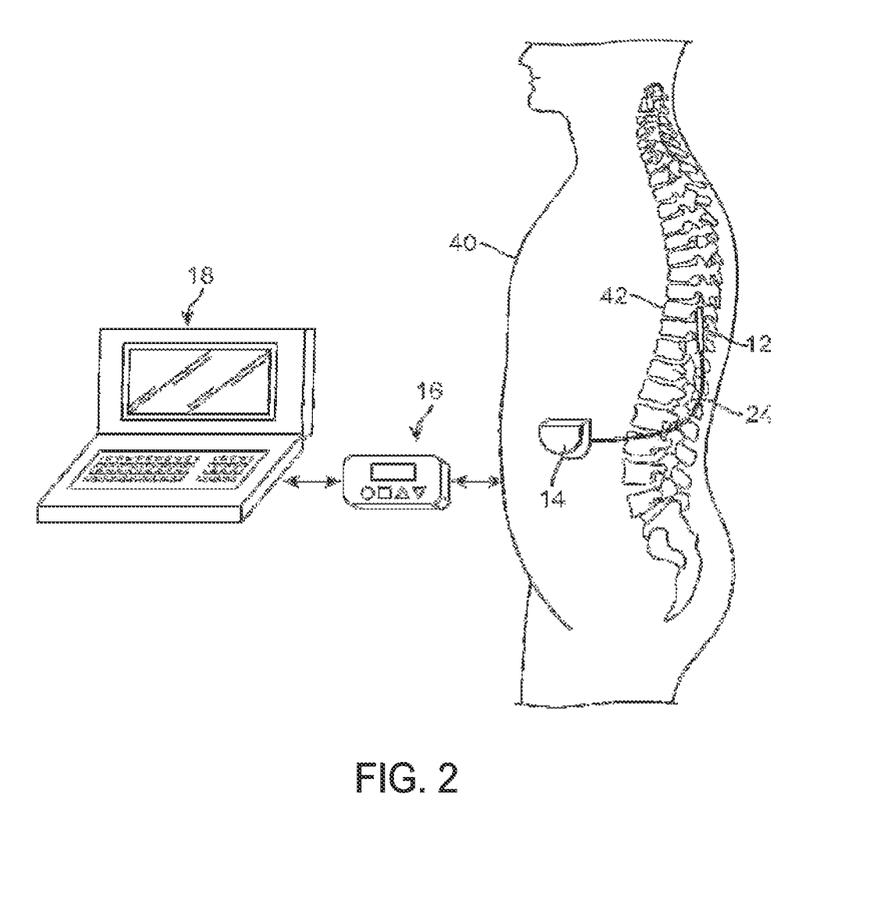
FIG. 2 is a plan view of the SCM system of FIG. 1 in use within a patient.

As shown in FIG. 2, the modulation leads 12 are implanted within the spinal column 42 of a patient 40. The preferred placement of the modulation leads 12 is adjacent, i.e., resting near, the spinal cord area to be stimulated. Due to the lack of space near the location where the modulation leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the modulation leads 12. As there shown, the CP 18 communicates with the IPG 14 via the RC 16.

Figure 3:
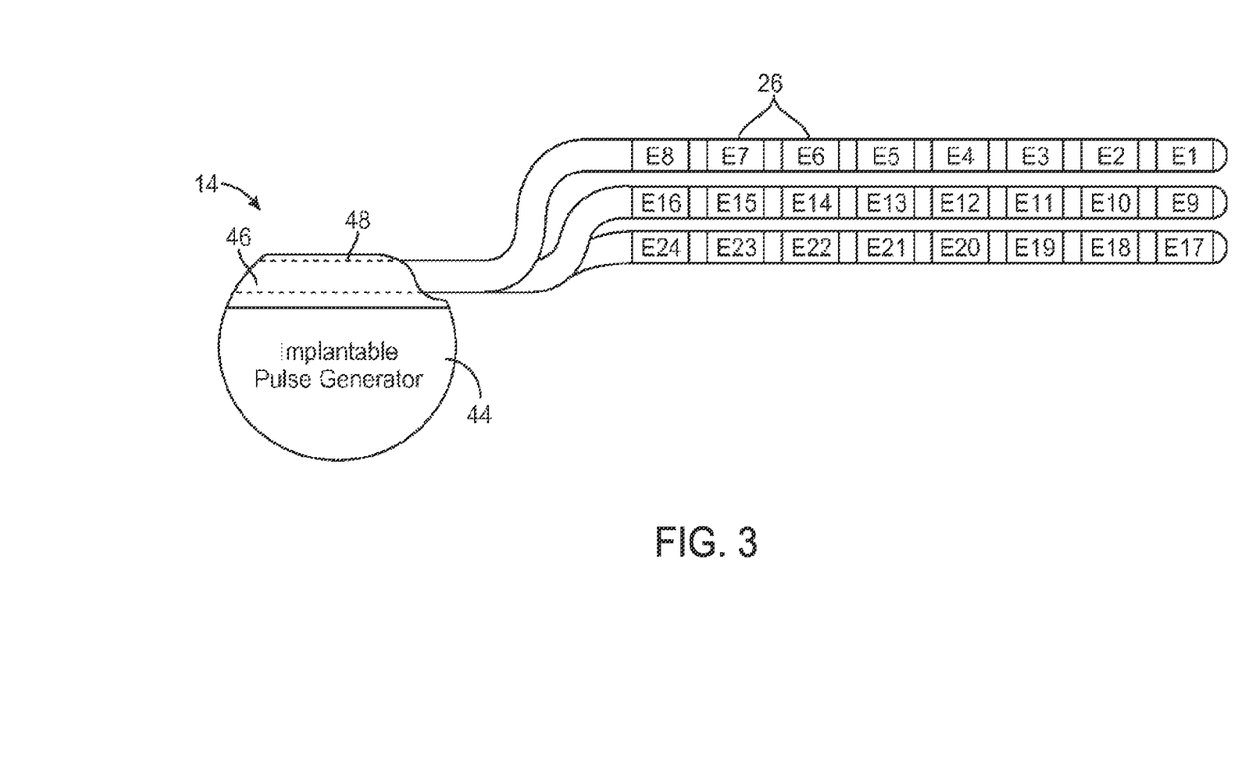
FIG. 3 is a plan view of an implantable pulse generator (IPG) and three percutaneous stimulation leads used in the SCM system of FIG. 1.

Referring now to FIG. 3, the external features of the modulation leads 12 and the IPG 14 will be briefly described. Each of the modulation leads 12 has eight electrodes 26 (respectively labeled E1-E8, E9-E16, and E17-E24). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Modulation lead for Neural Stimulation and Method of Making Same," the disclosures of which are expressly incorporated herein by reference.

Figure 4:
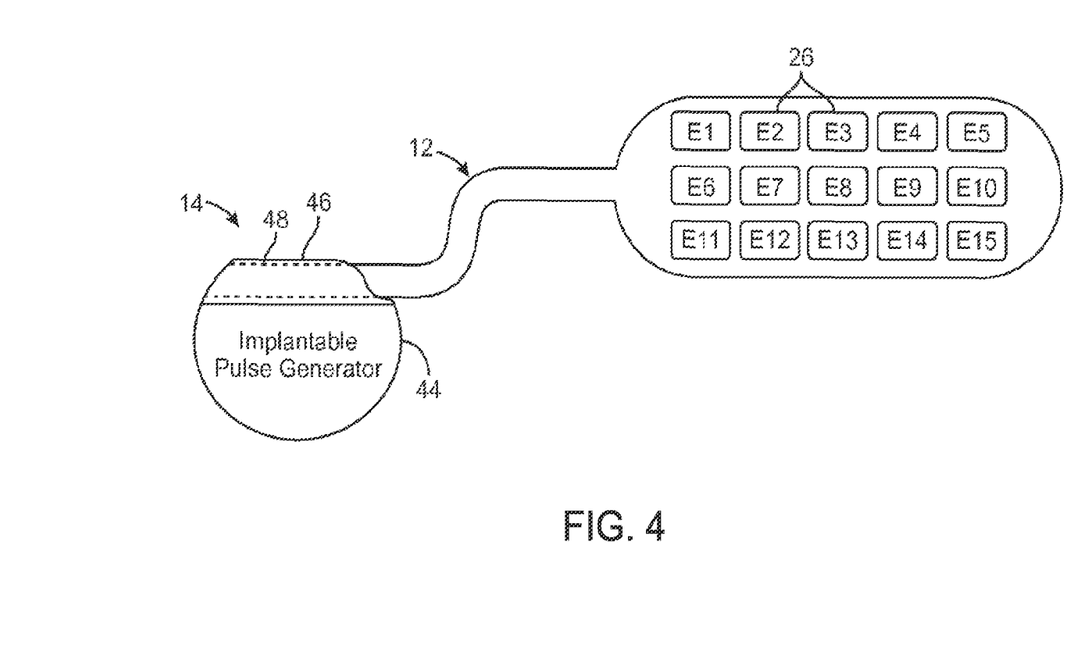
FIG. 4 is a plan view of an implantable pulse generator (IPG) and a surgical paddle lead used in the SCM system of FIG. 1.

Alternatively, as illustrated in FIG. 4, the modulation lead 12 takes the form of a surgical paddle lead on which electrodes 26 are arranged in a two-dimensional array in three columns (respectively labeled E1-E5, E6-E10, and E11-E15) along the axis of the modulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

In each of the embodiments illustrated in FIGS. 3 and 4, the IPG 14 comprises an outer case 44 for housing the electronic and other components (described in further detail below). The outer case 44 is composed of an electrically conductive, biocompatible material, such as titanium, and forms a hermetically sealed compartment wherein the internal electronics are protected from the body tissue and fluids. In some cases, the outer case 44 may serve as an electrode. The IPG 14 further comprises a connector 46 to which the proximal ends of the modulation leads 12 mate in a manner that electrically couples the electrodes 26 to the internal electronics (described in further detail below) within the outer case 44. To this end, the connector 46 includes one or more ports (three ports 48 or three percutaneous leads or one port for the surgical paddle lead) for receiving the proximal end(s) of the modulation lead(s) 12. In the case where the lead extensions 24 are used, the port(s) 44 may instead receive the proximal ends of such lead extensions 24.

The IPG 14 includes pulse generation circuitry that provides electrical modulation energy in the form of a pulsed electrical waveform to the electrode array 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the modulation on duration X and modulation off duration Y).

Electrical modulation will occur between two (or more) activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case 44 of the IPG 14, so that modulation energy is transmitted between the selected electrode 26 and the case 44. Bipolar modulation occurs when two of the lead electrodes 26 are activated as anode and cathode, so that modulation energy is transmitted between the selected electrodes 26. For example, an electrode on one lead 12 may be activated as an anode at the same time that an electrode on the same lead or another lead 12 is activated as a cathode. Tripolar modulation occurs when three of 15 the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The modulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) modulation pulse and an anodic (positive) recharge pulse that is generated after the modulation pulse to prevent direct current charge transfer through the tissue, thereby avoiding electrode degradation and cell trauma. That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the recharge pulse).

Figure 5:
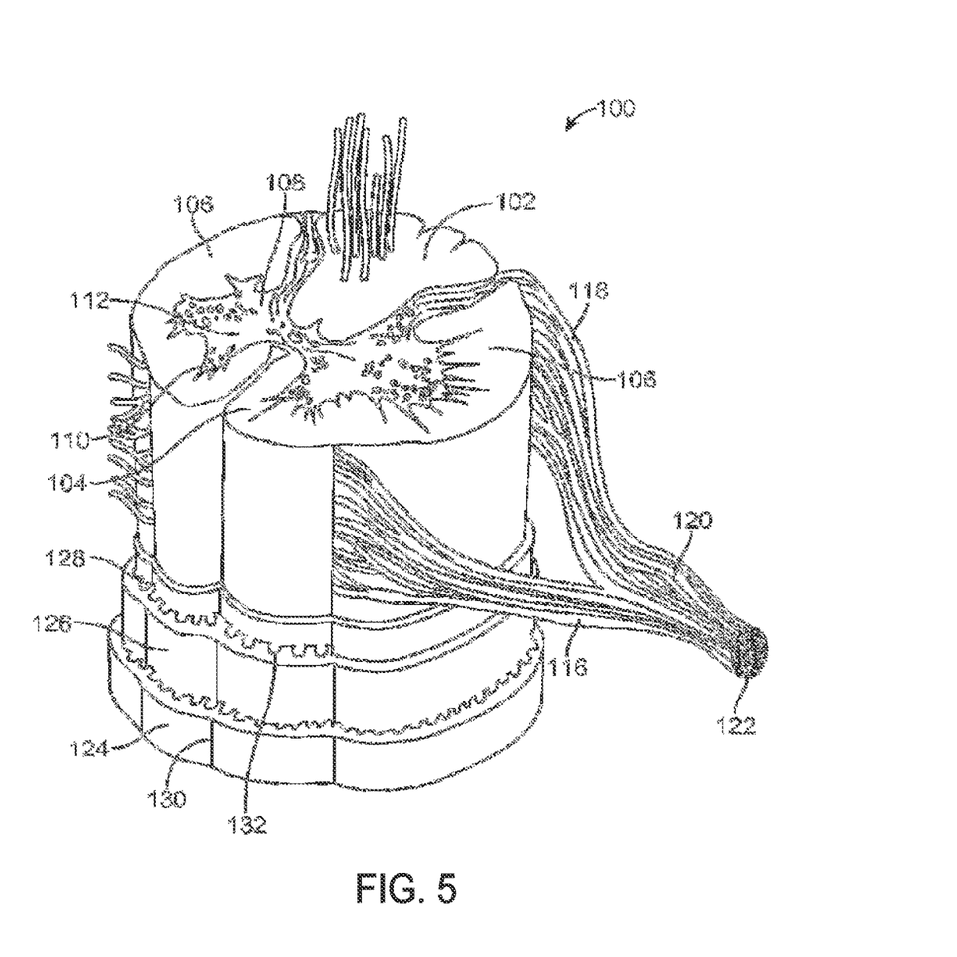
FIG. 5 is a perspective view of the spinal cord and spinal nerves.
Figure 6:
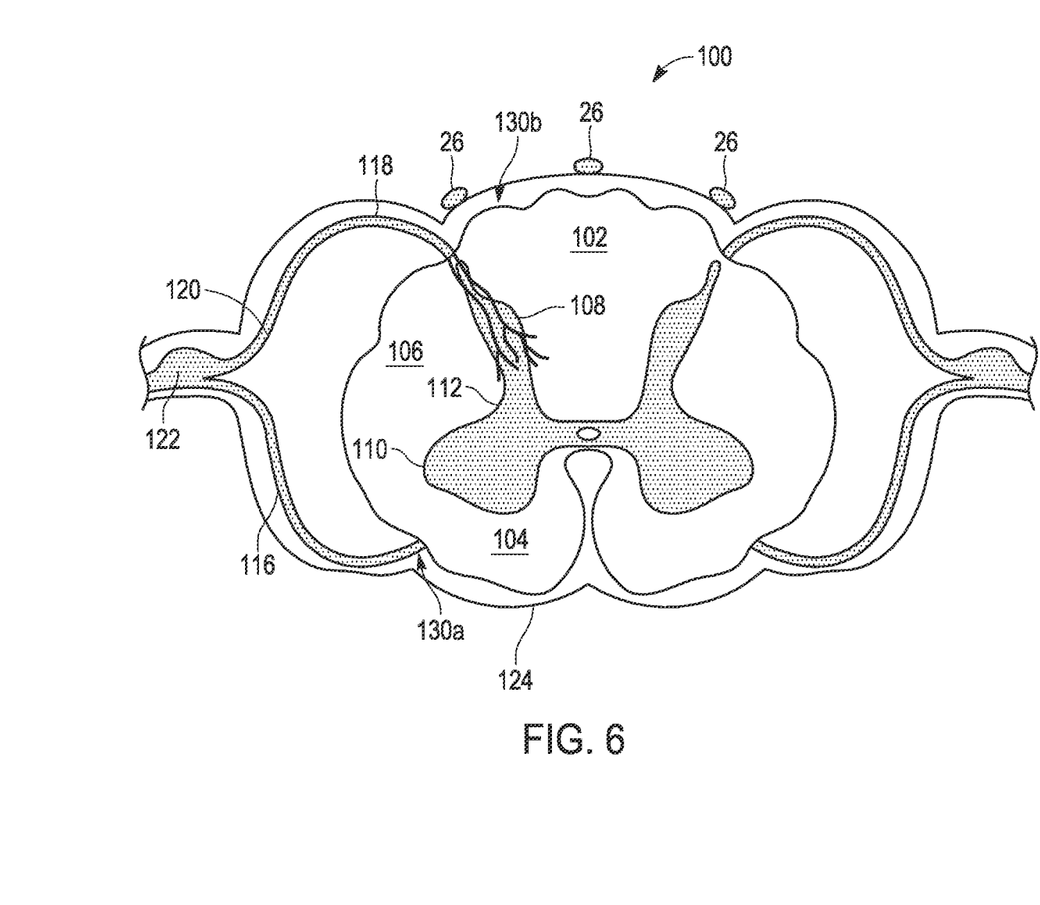
FIG. 6 is a cross-sectional view of the spinal cord showing an electrode arrangement relative to the spinal cord in accordance with a modulation regimen of the present inventions.
Figure 7:
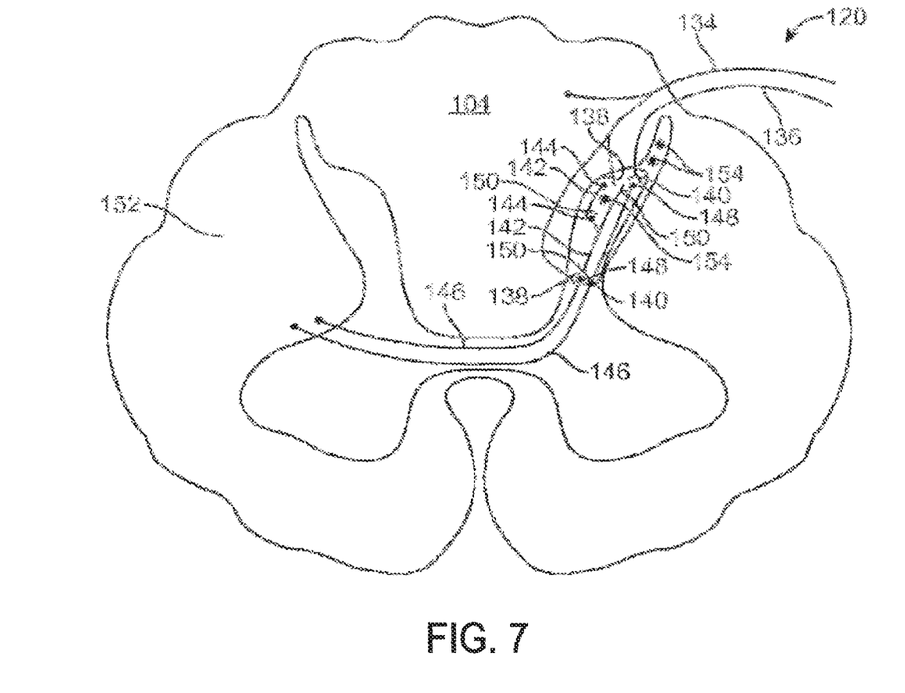
FIG. 7 is a cross-sectional view of the connection between the dorsal root fibers and the neural elements in the dorsal horn.

Referring now to FIGS. 5-7, the portions of the spinal cord 100 that are relevant to the present inventions will be described. The spinal cord 100 is divided into three functional columns: the dorsal column 102, the ventral column 104, and the lateral columns 106. Similarly, the butterfly-shaped gray matter of the spinal cord 100 is divided into the dorsal horn 108, the ventral horn 110, and the lateral horn 112.

A group of motor nerve rootlets (ventral root (VR) nerve fibers) 114 branch off of the ventral horn 110 and combine to form the ventral root 116. Similarly, a group of sensory nerve rootlets (dorsal root (DR) nerve fibers) 118 branch off of the dorsal horn 108 and combine to form the dorsal root 120. The dorsal root 120 and the ventral root 116 combine to form the spinal nerve 122, which innervates peripheral regions (e.g., arms, legs, etc.) of the patient's body. A number of spinal nerves branch off the spinal cord. In each patient, there are eight cervical spinal nerves designated C1-C8, twelve thoracic spinal nerves designated T1-T12, five lumbar spinal nerves designated L1-L5, and five sacral spinal nerves designated S1-S5. The spinal cord 100 is protected by three layers of connective tissue, the dura mater 124, the arachnoid 126, and the pia mater 128, collectively referred to as meninges. An epidural space 130 surrounds the dura mater 124, and a subararchnoid space 132 lies under the arachnoid 126. The epidural space 130 may be topologically divided into two halves: a ventral epidural space 130a and a dorsal epidural space 130b.

More relevant to the present inventions, the A-fiber afferents 134 of the dorsal root 120, which carry touch, pressure, pain, and temperature information, bifurcate between the dorsal column 102 and the dorsal horn 108 at nerve endings (or axon terminals) 138, whereas the C-fiber afferents 136 of the dorsal root 130, which carry pain and temperature information, terminate in the dorsal horn 108 at nerve endings (or axon terminals) 140. The nerve endings 138, 140 in the dorsal horn 108 synapse to nerve endings (or dendrites of cell bodies) 144 of interneurons 142 within the dorsal horn 108 and nerve endings (or dendrites of cell bodies) 148 of projection neurons 146. The interneurons 142 and projection neurons 146 can be referred to as "post-synaptic network neurons." The nerve endings (or axon terminals) 150 of the interneurons 142 may also synapse to the nerve endings (or dendrites of cell bodies) 148 of the projection neurons 146 and the nerve endings (or dendrites of cell bodies) 144 of other interneurons 142. The projection neurons 146 traverse the dorsal horn 108 and synapse to the dorsolateral funiculus 152 of the spinal cord 100, which in turn, projects to the brain. The nerve endings, interneurons, and projection neurons can be considered as "afferent neural elements" in the dorsal horn 108. The dorsal horn 108 additionally includes neuroglia 154, which are non-neuronal cells that maintain homeostasis, form myelin, and provide support and protection for neurons.

In conventional SCS techniques, electrical modulation energy is applied to the dorsal column 102 of the spinal cord 100 to treat chronic neuropathic pain, and accordingly, modulation leads are positioned in the dorsal epidural space 130b. Electrical stimulation is then applied to the dorsal column 102, which evokes action potentials that antidromically travel to the dorsal horn 108, which in turn, causes interneuronal activity within the dorsal horn 108 that inhibits pain signals traveling into the dorsal horn 108 via the dorsal root 120 innervating the pain region of the patient from being conveyed along the projection neurons 146, up through the dorsolateral funiculus 152 to the brain. However, as previously stated, stimulation of the large fibers in the dorsal column 102 evokes action potentials that orthodromically travel to the brain of the patient, thereby causing paresthesia, which may be painful or otherwise uncomfortable for the patient.

As opposed to the conventional SCS techniques, the methods of the present invention preferentially modulate the dorsal horn 108 relative to the dorsal column 102 of the spinal cord 100. In particular, as shown in FIG. 6, one or more electrodes 26 (only one shown) may be implanted within the dorsal epidural space 130b. In the case of unilateral pain, the electrodes 26 are preferably implanted within the dorsal epidural space 130b near the DR nerve fiber 118 iposilateml to the pain. In the case of bi-lateral pain the electrodes 26 may be implanted within the dorsal epidural space 130b as close to the anatomical midline as possible or may be implanted on opposite lateral sides of the dorsal epidural space 130b near DR nerve fibers 118. Thus, conveyance of electrical energy from the electrodes 26 will modulate the afferent neural elements in the dorsal horn 108, thereby treating the neuropathic pain via the afore-described gate control theory of pain. Alternatively or in addition to implantation of the electrodes 26 in the dorsal epidural space 130b, one or more electrodes 26 (not shown) may be implanted within the ventral epidural space 130a, in which case, conveyance of electrical energy from these electrodes 26 will modulate the efferent neural elements in the ventral horn 110, thereby inducing an endogenous opioid response within ventral horn 110 that treats any nociceptive pain, as described in U.S. Provisional Patent Application 61/704, 381, entitled "Method For Epidural Stimulation of Neural Structures," which is expressly incorporated herein by reference.

The electrical modulation energy may be applied by the electrodes 26 in a bipolar manner, but is preferably applied in a monopolar manner, so that the field strength of the electrical modulation energy decays at a relatively low rate with distance. As such, the electrode 26 may be relatively far from the dorsal horn 108 for the electrical energy to modulate the afferent neural elements within the dorsal horn 108. The modulation energy may be sub-threshold in that no action potentials are evoked in the dorsal horn 108, or the modulation energy may take the form of stimulation energy that evokes action potentials in the dorsal horn 108. But in either event, it is preferable that the DC column 104 not be stimulated (i.e., action potentials are not evoked in the dorsal column 104) in such a manner that would cause the patient to experience side-effects, and in this particular case, perceiving paresthesia. Other side-effects that are preferably avoided include inadvertent stimulation or blocking of motor nerve structures and/or interference of sensory motor structures other than those targeted for the treatment of the chronic pain.

Significantly, it has been discovered that the polarity and pulse width of an applied electrical modulation current are critical parameters for providing therapy to patient's suffering from chronic pain without causing the patient to perceive paresthesia. In particular, the delivery of electrical modulation current from a modulation lead 12 implanted within the dorsal epidural space 130b of a patient is known to provide pain relief to a patient without paresthesia. For example, the pulse width may be equal to or less than 200 µs, preferably equal to or less than 100 µs, and most preferably equal to or less than 50 µs. The pulse width may be greater than 10 µs. In an alternative embodiment, a train of closely spaced narrow pulses (e.g., 1 µs) can be conveyed in a manner that emulates a greater pulse width (e.g., 50 µs).

It is believed that, based on the theories set forth in U.S. patent application Ser. No. 13/197,949, entitled "Method for Selectively Performing Local and Radial Peripheral Stimulation," which is expressly incorporated by reference, the application of electrical modulation energy with a relatively small pulse width preferentially stimulates the nerve endings in the dorsal horn 108 over the dorsal column 104, which in turn, indirectly stimulates the interneurons and projection neurons in the dorsal horn 108, thereby invoking the afore-described gate control theory to relieve the pain. It is also believed that the interneurons and projections neurons, and possibly even the neuroglia, in the dorsal horn 108 may also be directly preferentially stimulated over the dorsal column 104. To maximize selectivity between the afferent neural elements in the dorsal horn 108 and the DC column 104, the applied electrical modulation current is anodic, although in some cases, the applied electrical modulation current may be cathodic. Significantly, the minimization or elimination of paresthesia can be accomplished in the absence of a high pulse rate, thereby minimizing energy consumption in the IPG 14. For example, the pulse rate may be less than 1500 Hz, and preferably less than 500 Hz.

To provide therapy to the patient without the perception of paresthesia, electrical modulation energy having a relatively large pulse amplitude may be initially delivered to the spinal cord 100, such that the DC column 104, along with the afferent neural elements in the dorsal horn 108, are modulated, thereby causing the patient to perceive paresthesia while receiving therapy. The pulse amplitude of the delivered electrical modulation energy may then be incrementally decreased (e.g., at 0.1 mA steps) until the perception of paresthesia disappears. At this point, even though the perception of paresthesia ceases, the patient will still be receiving therapy via the modulation of the afferent neural elements in the dorsal horn 108. Alternatively, electrical modulation energy having a relatively small pulse amplitude may be initially delivered to the spinal cord 100, such that the dorsal column 104 is not modulated, thereby avoiding a perception of paresthesia. The pulse amplitude of the delivered electrical modulation energy may then be incrementally increased (e.g., at 0.1 mA steps) until the dorsal column 104, along with the afferent neural elements of the dorsal horn 108, are modulated, thereby causing the patient to perceive paresthesia while receiving therapy. The pulse amplitude of the delivered electrical modulation energy may then be decreased by one incremental step, so that the perception of paresthesia disappears. In either case, the maximum number of afferent neural elements in the dorsal horn 108 may be modulated, thereby providing efficacious therapy to the patient, without modulating the dorsal column 104 that would otherwise cause the perception of paresthesia.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient using at least one electrode implanted within an epidural space in the patient for use in delivering a modulation field to spinal cord tissue in the patient, comprising:
preferentially modulating neural elements within a dorsal horn over dorsal column fibers to effectively deliver the therapy without causing patient-perceived paresthesia, including delivering pulsed electric current with a polarity, a pulse width, and an amplitude to provide the modulation field from the at least one electrode to the dorsal horn and to preferentially modulate the neural elements in the dorsal horn over the dorsal column fibers, the amplitude of the pulsed electric current being above a threshold for modulating the neural elements in the dorsal horn to be therapeutically effective and below a threshold for modulating the dorsal column fibers to avoid causing patient-perceived paresthesia, wherein preferentially modulating the neural elements within the dorsal horn includes delivering the pulsed electrical current at a defined pulse rate less than 1500 Hz from the at least one electrode within the epidural space into the spinal cord tissue of the patient.

2. The method of claim 1, wherein the pulsed electrical current is anodic.

3. The method of claim 1, wherein the pulsed electrical current is cathodic.

4. The method of claim 1, wherein the pulse width is equal to or greater than 10 μs.

5. The method of claim 1, wherein the pulse width is equal to or less than 200 μs.

6. The method of claim 1, wherein preferentially modulating neural elements within a dorsal horn includes evoking action potential in the dorsal horn.

7. The method of claim 1, wherein preferentially modulating neural elements within a dorsal horn includes delivering subthreshold modulation energy that does not evoke action potentials in the dorsal horn.

8. The method of claim 1, wherein preferentially modulating neural elements within the dorsal horn includes preferentially modulating nerve endings.

9. A method of providing therapy to a patient using at least one electrode implanted within an epidural space in the patient for use in delivering a modulation field to spinal cord tissue in the patient, comprising:
preferentially modulating neural elements within a dorsal horn over dorsal column fibers to effectively deliver the therapy without causing patient-perceived paresthesia, including delivering pulsed electric current with a polarity, a pulse width, and an amplitude to provide the modulation field to the dorsal horn to preferentially modulate the neural elements in the dorsal horn over the dorsal column fibers, the amplitude of the pulsed electric current being above a threshold for modulating the neural elements in the dorsal horn to be therapeutically effective and below a threshold for modulating the dorsal column fibers to avoid causing patient-perceived paresthesia, wherein preferentially modulating the neural elements within the dorsal horn includes delivering the pulsed electrical current from the at least one electrode within the epidural space into a spinal cord tissue of the patient, the pulsed electrical current having a defined pulse width equal to or less than 200 μs and a defined pulse rate less than 1500 Hz.

10. The method of claim 9, wherein the pulse width is equal to or greater than 10 μs.

11. The method of claim 9, wherein the pulse width is equal to or less than 50 μs.

12. The method of claim 9, wherein the pulse width is less than 100 μs.

13. The method of claim 9, wherein the pulsed electrical current is anodic.

14. The method of claim 9, wherein the pulsed electrical current is cathodic.

15. A system, comprising:
at least one modulation lead with at least one modulation electrode configured to be implanted within an epidural space in a patient for use in delivering a modulation field to spinal cord tissue in the patient; and
an implantable pulse generator configured to connect to the at least one lead, the implantable pulse generator including a programmed set of modulation parameters to use the at least one modulation electrode within the epidural space to preferentially modulate neural elements within a dorsal horn over dorsal column fibers to effectively deliver a therapy without causing patient-perceived paresthesia, the programmed set of modulation parameters including parameters for delivering pulsed electrical current with a polarity, a pulse width, and an amplitude to provide the modulation field from the at least one electrode to the dorsal horn and to preferentially modulate the neural elements in the dorsal horn over the dorsal column fibers, the amplitude of the pulsed electric current being above a threshold for modulating the neural elements in the dorsal horn to be therapeutically effective and below a threshold for modulating the dorsal column fibers to avoid causing patient-perceived paresthesia, the pulsed electrical current having a defined pulse rate less than 1500 Hz from the at least one electrode within the epidural space into the spinal cord tissue of the patient.

16. The system of claim 15, wherein the pulse width is within a pulse width range extending from 10 μs to 200 μs.

17. The system of claim 16, wherein the pulse width is equal to or less than 100 μs.

18. The system of claim 15, wherein the programmed set of modulation parameters includes parameters for delivering pulsed electrical current to evoke action potential in the dorsal horn.

19. The system of claim 15, wherein the programmed set of modulation parameters includes parameters for delivering subthreshold modulation energy that does not evoke action potentials in the dorsal horn.

20. The system of claim 15, wherein the pulse width is equal to or less than 50 μs.

* * * * *

UNITED STATES PATENT AND TRADEMARK OFFICE
CERTIFICATE OF CORRECTION

PATENT NO. : 10,159,837 B2  
APPLICATION NO. : 14/679993  
DATED : December 25, 2018  
INVENTOR(S) : Lee et al.

Page 1 of 1

It is certified that error appears in the above-identified patent and that said Letters Patent is hereby corrected as shown below:

In the Specification

In Column 6, Line 52, delete "subararchnoid" and insert --subarachnoid-- therefor In Column 6, Line 61, delete "130," and insert --120,-- therefor In Column 7, Line 36, delete "(only one shown)"

In Column 8, Line 4, delete "104" and insert --102-- therefor

In Column 8, Line 6, delete "104)" and insert --102)-- therefor

In Column 8, Line 33, delete "104," and insert --102,-- therefor

In Column 8, Line 40, delete "104." and insert --102.-- therefor

In Column 8, Line 41, delete "104," and insert --102,-- therefor

In Column 8, Line 52, delete "104," and insert --102,-- therefor

In Column 8, Line 64, delete "104" and insert --102-- therefor

In Column 8, Line 67, delete "104," and insert --102,-- therefor

In Column 9, Line 9, delete "104" and insert --102-- therefor

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*